(12) United States Patent
Bae et al.

(10) Patent No.: US 11,071,457 B2
(45) Date of Patent: Jul. 27, 2021

(54) APPARATUS AND METHOD FOR REMOVING STRANDS OF HAIR FROM NEAR-INFRARED SPECTROSCOPY

(71) Applicant: Korea Advanced Institute of Science and Technology, Daejeon (KR)

(72) Inventors: Hyeon Min Bae, Seoul (KR); Jae Myoung Kim, Daejeon (KR); Jong Kwan Choi, Daejeon (KR); Min Gyu Choi, Daejeon (KR); Gun Pil Hwang, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 702 days.

(21) Appl. No.: 15/523,170

(22) PCT Filed: Nov. 14, 2014

(86) PCT No.: PCT/KR2014/010961
§ 371 (c)(1),
(2) Date: Jun. 28, 2017

(87) PCT Pub. No.: WO2016/068374
PCT Pub. Date: May 6, 2016

(65) Prior Publication Data
US 2017/0319072 A1    Nov. 9, 2017

(30) Foreign Application Priority Data
Oct. 30, 2014   (KR) .................... 10-2014-0149067

(51) Int. Cl.
*A61B 5/00*      (2006.01)
*G01J 3/28*      (2006.01)
(Continued)

(52) U.S. Cl.
CPC .......... *A61B 5/0075* (2013.01); *A61B 5/0042* (2013.01); *A61B 5/6803* (2013.01);
(Continued)

(58) Field of Classification Search
CPC ... A61B 5/0075; A61B 5/6803; A61B 5/6814; A61B 5/1455; A61B 5/14551; A61B 5/14552; A61B 5/14553
See application file for complete search history.

(56) References Cited

U.S. PATENT DOCUMENTS 5,099,842 A * 3/1992 Mannheimer ...... A61B 5/04485
600/323
6,618,614 B1 * 9/2003 Chance .............. A61B 5/14551
600/473
(Continued)

FOREIGN PATENT DOCUMENTS

| JP | 05093403 U | 12/1993 |
|---|---|---|
| JP | 2009082265 A | 4/2009 |
| KR | 1020050110573 A | 11/2005 |

OTHER PUBLICATIONS

International Search Report issued in International Patent Application No. PCT/KR2014/010961, dated Jul. 27, 2015, 2 pages.

*Primary Examiner* — Chu Chuan Liu
(74) *Attorney, Agent, or Firm* — Dinsmore & Shohl LLP; Yongsok Choi, Esq.

(57) ABSTRACT

Disclosed are an apparatus and a method for removing strands of hair from a near-infrared spectroscopy. The apparatus for removing strands of hair from a near-infrared spectroscopy may comprise: an arch-shaped main body worn on the head of a user, having a plurality of protrusions formed at an inner side part of the arch-shaped main body, and configured to expose a portion of scalp by arranging the strands of hair; a probe configured to come into close contact
(Continued)

with the scalp; and a sensor configured to be accommodated inside the probe and receive light.

4 Claims, 9 Drawing Sheets

(51) Int. Cl.
    *G01N 21/25*     (2006.01)
    *A61B 6/00*     (2006.01)

(52) U.S. Cl.
    CPC .............. *A61B 5/6814* (2013.01); *A61B 6/00* (2013.01); *G01J 3/28* (2013.01); *G01N 21/25* (2013.01)

(56) References Cited

U.S. PATENT DOCUMENTS

| | | | | |
|---|---|---|---|---|
| 7,039,454 | B1* | 5/2006 | Kaga | A61B 5/1455 |
| | | | | 324/96 |
| 7,974,671 | B2* | 7/2011 | Fujiwara | A61B 5/0042 |
| | | | | 600/344 |
| 8,103,332 | B2* | 1/2012 | Kiguchi | A61B 5/1455 |
| | | | | 600/476 |
| 2009/0088649 | A1* | 4/2009 | Ninomiya | A61B 5/0059 |
| | | | | 600/476 |
| 2013/0116521 | A1* | 5/2013 | Inoue | G01N 21/359 |
| | | | | 600/328 |

\* cited by examiner

APPARATUS AND METHOD FOR REMOVING STRANDS OF HAIR FROM NEAR-INFRARED SPECTROSCOPY

FIELD OF THE INVENTION

The present invention relates to an apparatus and a method for removing strands of hair from a near-infrared spectroscopy. More particularly, the present invention relates to an apparatus and a method for removing strands of hair from a near-infrared spectroscopy, which are capable of removing the strands of hair and exposing scalp to make a probe come into close contact with the scalp.

BACKGROUND

Near-infrared light is an electromagnetic wave having a wavelength range (approximately 1.5 to 0.75 μm) in infrared light, which is close to a visible light.

A conventional measuring instrument using such near-infrared light may be configured to include a near-infrared light sensor part having a light emitting sensor and a light receiving sensor, an amplifier, a measurement part, an analog/digital (A/D) converter, a micro controller unit (MCU), and a driver. When the light emitting sensor irradiates a body of a user with near-infrared light under the control of a central processing unit and the driver, a portion of the near-infrared light may be absorbed into the body of the user and the remaining portion thereof may be reflected and collected to the light receiving sensor. The collected near-infrared light may be converted into an electrical signal, and the electrical signal may be amplified through the amplifier, transmitted to the measurement part, and processed in the central processing unit.

However, the removal of strands of hair is very important for equipment which measures a brain activation image using near-infrared light (NIR). Since the near-infrared light has very low transmittance with respect to the strands of hair, attaching a light source and a sensor probe to a head without removing the strands of hair may cause a big obstacle in extracting desired signals.

For this reason, it is very important for a process of pushing strands of hair out to expose scalp and enabling a probe to come into close contact with the scalp.

SUMMARY OF THE INVENTION

An objective of the present invention is to provide an apparatus and a method for removing strands of hair from a near-infrared spectroscopy, which are capable of efficiently extracting a signal by exposing scalp and enabling a probe to come into close contact with the scalp using the apparatus for removing strands of hair from the near-infrared spectroscopy.

Another objective of the present invention is to provide an apparatus and a method for removing strands of hair from a near-infrared spectroscopy, which are capable of efficiently measuring a brain activation image by forming a structure having a shape which enables a probe form to reach up to scalp, and by increasing an area in which the probe form comes into contact with the scalp.

According to one aspect of the present invention, an apparatus for removing strands of hair from a near-infrared spectroscopy comprises an arch-shaped main body worn on a head of a user, having a plurality of protrusions formed at an inner side part the arch-shaped main body, and configured to expose a portion of scalp by separating the strands of hair; and a probe configured to accommodate a sensor thereinside and come into close contact with the scalp.

According to another aspect of the present invention, the probe may be formed in plural number and may be respectively disposed in rear of the plurality of protrusions.

According to another aspect of the present invention, in the arch-shaped main body, a plurality of holes may be respectively formed in rear of the plurality of protrusions and the probes may be respectively coupled to the plurality of holes in an insertion manner.

According to another aspect of the present invention, the sensor may be configured with a rectangular printed circuit board (PCB) in which a vertical length is longer than a horizontal length.

According to another aspect of the present invention, a wedge-shaped optical probe for removing strands of hair comprises a cylindrical main body configured to accommodate a sensor thereinside; at least one wedge-shaped surface formed at a lower end part of the cylindrical main body, wherein the wedge-shaped optical probe is configured to expose a portion of scalp of a user by separating the strands of hair to both sides along the at least one wedge-shaped surface, and to come into contact with the exposed portion of the scalp.

According to another aspect of the present invention, the wedge-shaped optical probe may further comprise a head part formed at an upper end part of the cylindrical main body and having a diameter that is greater than that of the cylindrical main body.

According to another aspect of the present invention, at least one wedge-shaped surface may be provided in a direction same as that in which the strands of hair are arranged, at least one wedge-shaped surface may be pushed and inserted between the separated strands of hair to expose the portion of the scalp, the cylindrical main body may be rotated to dispose and fix the at least one wedge-shaped surface to be perpendicular to a direction in which the strands of hair are arranged, and the head part may be exposed to the outside.

According to another aspect of the present invention, a toothbrush-shaped optical probe for removing strands of hair comprises a main body configured to accommodate a sensor; and a light guide provided with a plurality of threads at a lower end part of the main body, each of which enables light to be transmitted, and provided with a depression between adjacent threads among the plurality of threads, which is capable of accommodating the strands of hair, and coming into close contact with scalp of a user.

According to another aspect of the present invention, the light guide may be formed with acrylic optical fiber.

According to another aspect of the present invention, an outer circumferential surface of the light guide may prevent the light from being transmitted, and a leading end part of the light guide may enable the light to be transmitted.

According to another aspect of the present invention, a method for removing strands of hair using an apparatus for removing strands of hair from a near-infrared spectroscopy comprises steps of wearing an arch-shaped main body on a head of a user and exposing a portion of scalp by separating the strands of hair through a plurality of protrusions formed at an inner side part of an arch-shaped main body when wearing the arch-shaped main body; and enabling a cylindrical probe to come into close contact with the exposed portion of the scalp.

According to another aspect of the present invention, a method for removing strands of hair using a wedge-type optical probe for removing strands of hair comprises steps of exposing a portion of scalp by providing a wedge-shaped surface of the wedge-type optical probe in a direction in which the strands of hair are arranged, pushing and inserting the wedge-shaped surface between the strands of hair, and arranging the strands of hair to both sides; and rotating the wedge-type optical probe to provide and fix the wedge-shaped surface to be perpendicular to the direction in which the strands of hair are arranged.

According to the embodiments of the present invention, there may be provided an apparatus and a method for removing strands of hair from a near-infrared spectroscopy, which are capable of efficiently extracting a signal by exposing scalp and enabling a probe to come into close contact with the scalp using the apparatus for removing strands of hair from the near-infrared spectroscopy.

According to the embodiments of the present invention, there may be provided an apparatus and a method for removing strands of hair from a near-infrared spectroscopy, which are capable of efficiently measuring a brain activation image by forming a probe to have a shape which can reach up to scalp and increasing an area in which the probe comes into contact with the scalp.

DETAILED DESCRIPTION OF THE PREFERRED EMBODIMENTS

Hereinafter, embodiments of the present invention will be described in detail with reference to the accompanying drawings.

The removal of strands of hair is very important for equipment which measures a brain activation image using near-infrared light. Since the near-infrared light has very low transmittance with respect to the strands of hair, attaching a light source and a sensor probe to a head without completely removing the strands of hair may cause a big obstacle in extracting of desired signals.

Accordingly, the present invention proposes an apparatus for removing strands of hair and probes in the form of various shapes and thus a signal may be efficiently measured by removing the strands of hair.

Figure 1:
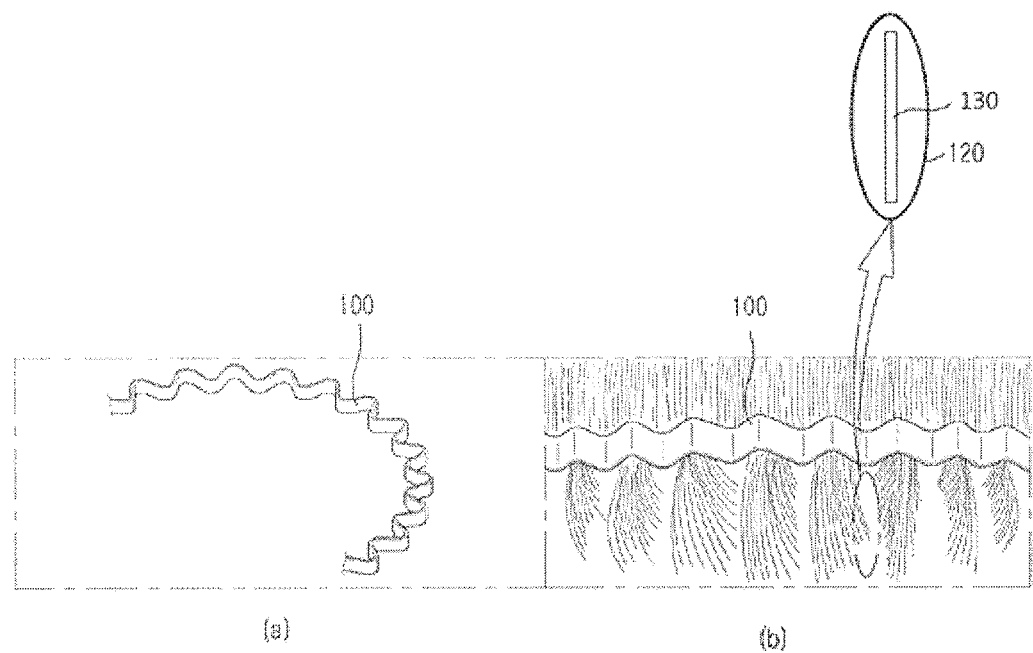
FIG. 1 shows an apparatus for removing strands of hair according to one embodiment of the present invention.

FIG. 1 shows an apparatus for removing strands of hair according to one embodiment of the present invention.

FIG. 1(a) illustrates a shape of a headband main body 100 which is on the market. When a forehead portion is scanned as targeting a frontal lobe with a structure, which has such a shape and is included in a brain imaging device, using near-infrared light, strands of hair on the forehead portion may be removed. Such a structure may also be used as a tool for removing strands of hair on another portion of a head in addition to the frontal lobe.

FIG. 1(b) illustrates a state in which the headband main body 100 is worn on a head of a user, and, as illustrated, the strands of hair is removed in the form of a valley.

Therefore, when scalp is exposed between the strands of hair and a structure of a probe 120, which is in the form of a streamlined shape, is inserted therebetween, the probe 120 may come into exact contact with the scalp with no interference of the strands of hair.

Further, since a sensor 130 configured to receive light should comprise an amplifier circuit stage, it may be configured with a thin printed circuit board (PCB). Here, the sensor 130 has a characteristic in which a horizontal length of a cross section of the PCB is shorter whereas a vertical length thereof is longer, so that the probe 120 accommodating the sensor 130 may be configured with an external structure in the form of the streamlined shape as shown in the drawing. The probe 120 having such a shape may be exactly inserted between the strands of hair which are removed by the headband main body 100.

Figure 2:
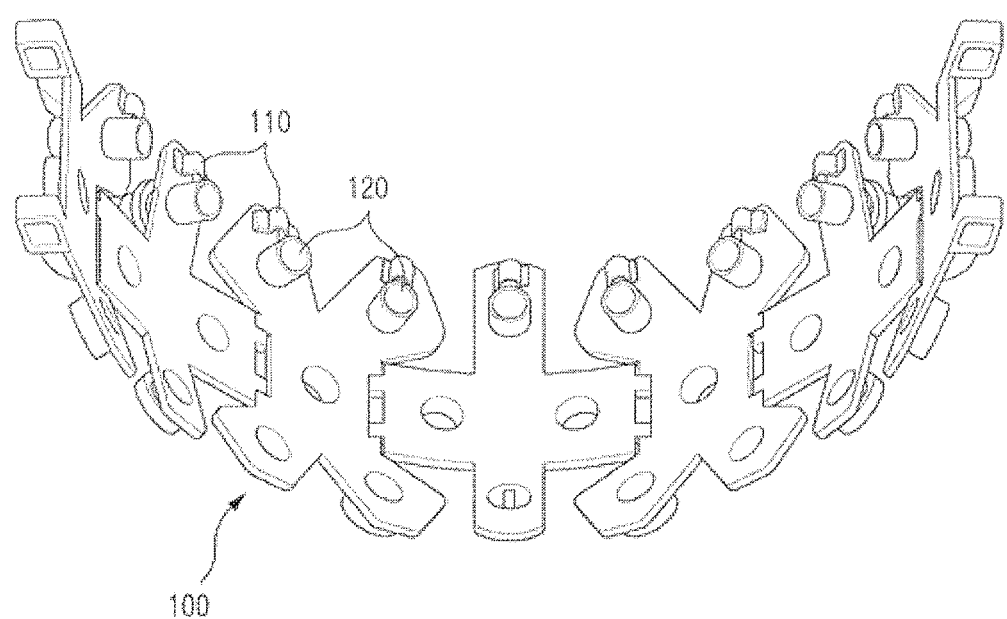
FIG. 2 shows an apparatus for removing strands of hair from a near-infrared spectroscopy according to one embodiment of the present invention.

FIG. 2 shows an apparatus for removing strands of hair from a near-infrared spectroscopy (NIRS) according to one embodiment of the present invention.

Referring to FIG. 2, the apparatus for removing strands of hair from a near-infrared spectroscopy (NIRS) may comprise a main body 100 and a probe 120. This illustrates that the structure shown in FIG. 1 is applied to an imaging apparatus using near-infrared light.

The main body 100 is configured in the form of an arch shape and worn on the head of the user in a manner of a headband.

Further, a plurality of protrusions 110 may be formed at an inner side part of the main body 100 and thus the strands of hair of the user may be arranged when the user wears the main body 100 such that a portion of scalp may be exposed. In other words, when the main body 100 is worn on the head of the user in a manner same as that of the headband, the strands of hair are upwardly swept and then separated to both sides of each of the plurality of protrusions 110 such that the portion of the scalp of the user may be exposed.

Furthermore, in the main body 100, a plurality of holes may be respectively formed in rear of the plurality of protrusion 110, and the probe 120 may be coupled to each of the plurality of holes in an insertion manner. At this point, a large number of holes are formed at the main body 100 so that a position, at which the probe 120 is coupled to each of the plurality of holes in an insertion manner, may be changed according to a user and the usage.

The probe 120 (or an optical probe) may accommodate a sensor thereinside, and may come into close contact with the exposed portion of the scalp by the plurality of protrusions 110. There is no limitation in shape of the probe 120, but the probe 120 may be preferable to be configured in the form of a streamlined shape so as to come into close contact with the exposed scalp. Here, the probe 120 may be a structure in the form of a cylinder shape, which surrounds a printed circuit board (PCB) including a transimpedance amplifier (TIA).

Further, a plurality of probes 120 may be formed, and each of the plurality of probes 120 may be respectively disposed in rear of the plurality of protrusions 110. Therefore, the plurality of protrusions 110 formed at the main body 100 remove the strands of hair, and each of the streamlined-shaped probes 120 including sensors thereinside is disposed between the removed strands of hair.

Furthermore, the sensors may be respectively accommodated inside the probes 120 and may receive light. Each of the sensors may comprise a PCB in a rectangular shape in which a vertical length is longer than a horizontal length, and the probes 120 may also be configured in the form of a streamlined shape in which a vertical length is longer than a horizontal length. That is, the probe structure in the form of a streamlined shape may be used to correspond to a PCB structure of the sensor so that the scalp may be exposed by removing the strands of hair from a portion of the scalp. Here, the PCB of the sensor may be designed to adhere in close proximity to the sensor for minimizing external noise.

Accordingly, the arch-shaped headband structure configured to remove upper strands of hair of the user is provided at an upper portion of the probe, and the probe is located directly below the headband structure, so that the probe may be disposed at a position at which the headband structure first passes over the strands of hair.

Such a structure may remove the strands of hair and enable the probe to come into close contact with the scalp when the headband structure is worn while sweeping up hair in a direction opposite to the strand of hair, at not only a forehead but also another portion of a head.

A method for removing strands of hair using the apparatus for removing strands of hair from such a near-infrared spectroscopy may comprise steps of wearing an arch-shaped main body on a head of a user and exposing a portion of scalp by arranging the strands of hair through a plurality of protrusions formed at an inner side part of an arch-shaped main body when wearing the arch-shaped main body; and enabling a cylindrical probe to come into close contact with the exposed portion of the scalp.

In the apparatus and the method for removing strands of hair on the scalp using the arch-shaped headband structure, the arch-shaped main body 100 may be used in not only a form integrated with the probe 120 and the sensor but also a form in which the main body 100 and the probe 120 are respectively separately provided to arrange the strands of hair and then the apparatus is worn over the arranged strands of hair.

Figure 3:
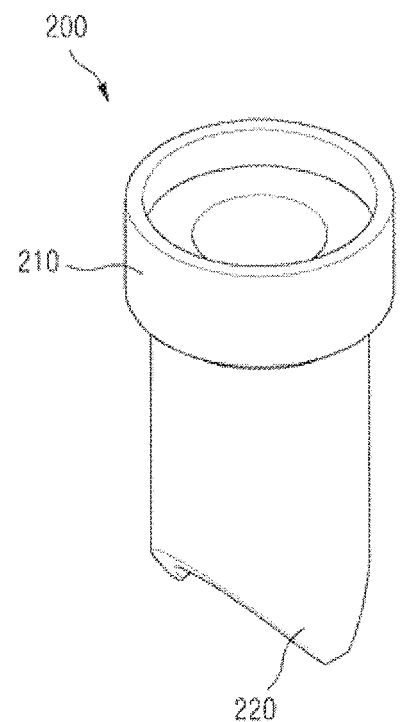
FIG. 3 is a perspective view of a wedge-shaped optical probe for removing strands of hair according to one embodiment of the present invention.

FIG. 3 is a perspective view of a wedge-shaped optical probe for removing strands of hair according to one embodiment of the present invention.

Referring to FIG. 3, a wedge-shaped optical probe 200 for removing strands of hair from a near-infrared spectroscopy (NIRS) may comprise a cylindrical main body, a head part 210, and a wedge-shaped surface 220.

The cylindrical main body may be configured in the form of a cylindrical shape and may accommodate a sensor thereinside.

The head part 210 is formed at an upper end part of the cylindrical main body, and a diameter of the head part 210 may be formed to be greater than that of the cylindrical main body.

At least one wedge-shaped surface 220 may be formed at a lower end part of the cylindrical main body. Preferably, two wedge-shaped surfaces 220 may be configured to face to each other. Accordingly, strands of hair may be separated to both sides along the wedge-shaped surfaces 220 and thus a portion of scalp of a user may be exposed, so that the cylindrical main body and the wedge-shaped surfaces may come into close contact with the exposed portion of the scalp.

Further, the wedge-shaped surface 220 is provided in a direction the same as the arrangement direction of the strands of hair and pushed therebetween to expose the portion of the scalp, and the cylindrical main body is rotated to dispose and fix the wedge-shaped surface 220 to be perpendicular to a direction in which the strands of hair are arranged, and thus the head part 210 can be exposed to the outside.

Furthermore, the sensor may be accommodated inside the cylindrical main body and may receive light. Further, the sensor may comprise an amplifier module PCB.

Figure 4:
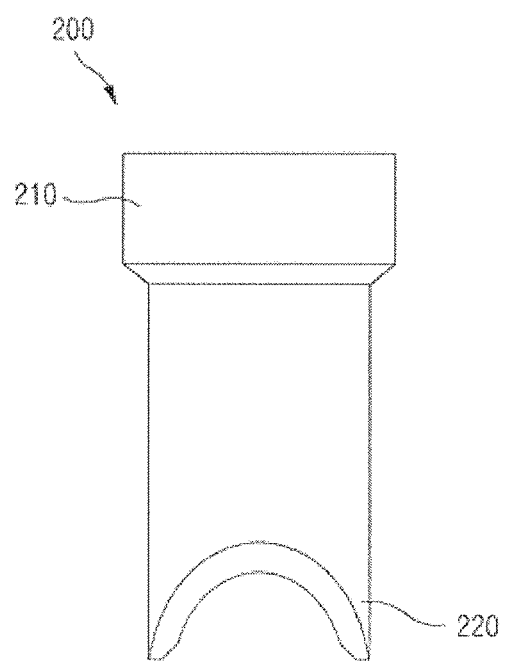
FIG. 4 is a front view illustrating the wedge-shaped optical probe for removing strands of hair according to one embodiment of the present invention.

FIG. 4 is a front view of the wedge-shaped optical probe for removing strands of hair according to one embodiment of the present invention.

Figure 5:
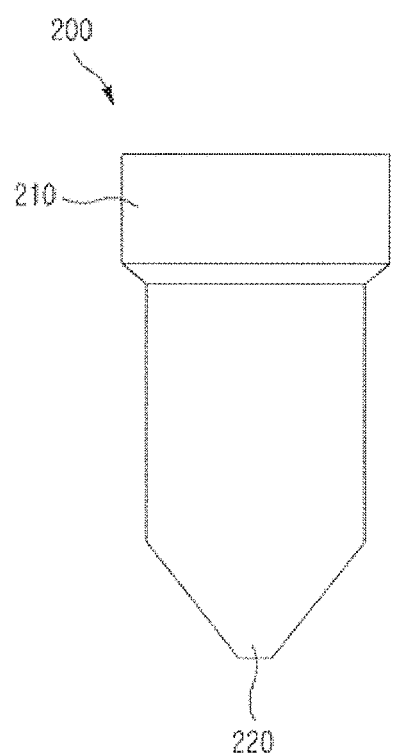
FIG. 5 is a lateral view illustrating the wedge-shaped optical probe for removing strands of hair according to one embodiment of the present invention.

FIG. 5 is a lateral view of the wedge-shaped optical probe for removing strands of hair according to one embodiment of the present invention.

Referring to FIGS. 4 and 5, a probe in the form of a wedge shape, which will be described below, may be proposed to come into close contact with scalp by avoiding the strands of hair, and, in a wedge-shaped optical probe for removing the strands of hair, at least one wedge-shaped surface 220 may be formed at a lower end part of the cylindrical main body and may separate the strands of hair to both sides along the wedge-shaped surface 220 to expose a portion of scalp of a user, and thus the cylindrical main body and the wedge-shaped surface 220 may come into close contact with the exposed portion of the scalp.

The at least one wedge-shaped surface 220 may be preferably configured in the form in which two wedge-shaped surfaces 220 face to each other, hair may be separated using the wedge-shaped surfaces 220, and the wedge-shaped surfaces 220 may be fixed by being rotated and opening a gap of the separated hair.

In other words, to remove densified strands of hair, the wedge-shaped surfaces are provided in a direction the same as that of the strands of hair and then are pushed and inserted between the strands of hair, and the probe is rotated to provide the wedge-shaped surfaces to be perpendicular to a direction in which the strands of hair are arranged when the wedge-type probe structure, which is pushed and inserted between the strands of hair, is inserted into the strands of hair by a predetermined depth, so that the strands of hair may be fixed in a state of being separated in left and right directions without returning to their original positions.

Such a wedge-shaped optical probe for removing strands of hair may be used in the range capable of covering an entire head.

FIG. 6 shows a method for removing strands of hair using the wedge-shaped optical probe for removing strands of hair according to one embodiment of the present invention.

The method for removing strands of hair using the wedge-shaped optical probe 200 for removing strands of hair, which has been described in FIGS. 3 to 5, will be described in detail below.

Figure 6A:
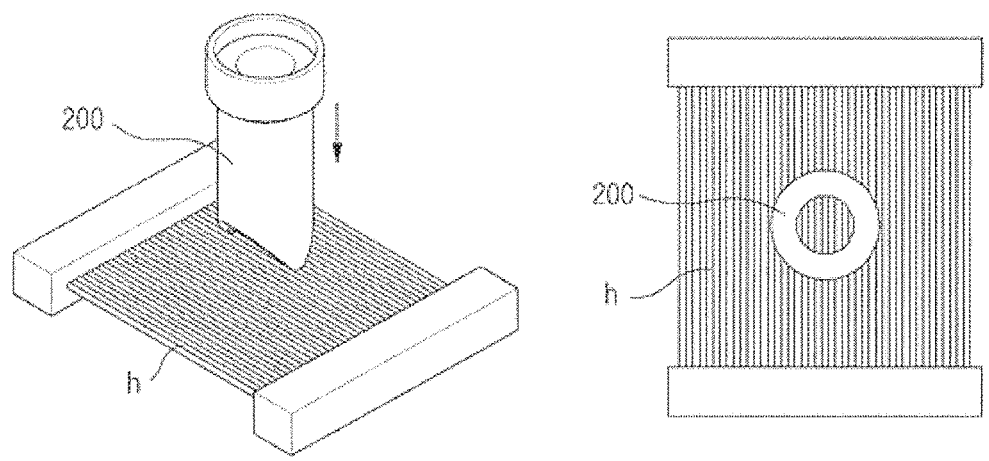
FIG. 6 shows a method for removing strands of hair using the wedge-shaped optical probe for removing strands of hair according to one embodiment of the present invention.

Referring to FIG. 6A, the wedge-shaped surfaces 220 of the wedge-shaped optical probe 200 may be disposed in a direction the same as that in which strands of hair h are arranged and may be pushed and inserted between the strands of hair h to separate the strands of hair h to both sides, thereby exposing a portion of scalp.

Figure 6B:
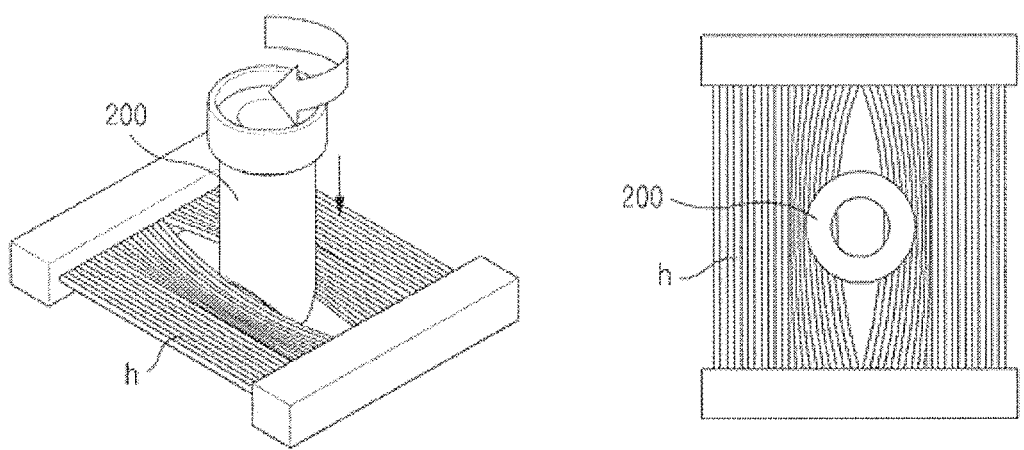

Referring to FIG. 6B, the strands of hair h may be separated to expose the portion of the scalp and then the wedge-type optical probe 200 may be rotated to dispose and fix the wedge-shaped surfaces 220 to be perpendicular to the direction in which the strands of hair h are arranged.

Figure 6C:
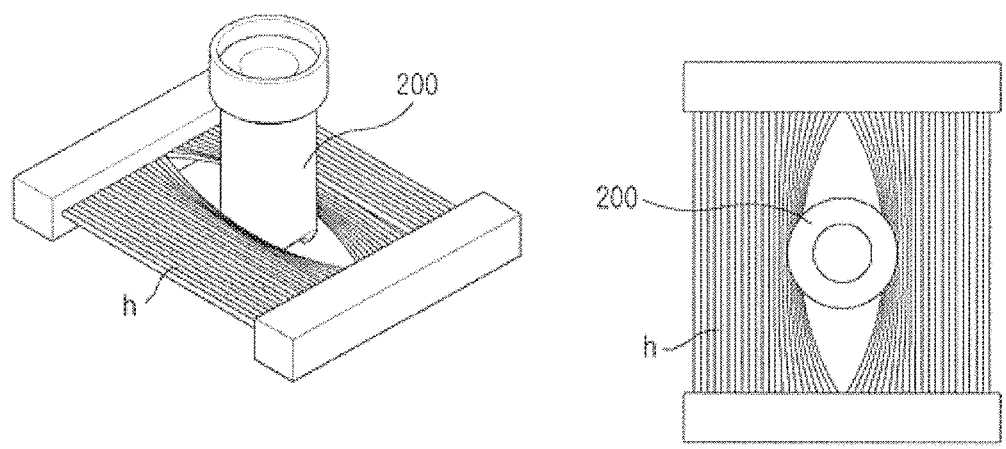

Referring to FIG. 6C, the wedge-shaped optical probe 200 may be fixed in a space between the strands of hair h, and the head part 210 may be exposed to the outside.

That is, the wedge-shaped optical probe 200 separates the strands of hair h along the wedge-shaped surfaces 220, the cylindrical main body comes into close contact with the scalp to be fixed to the separated strands of hair h, the head part 210 is exposed to the outside, so that the gripping of the user can be facilitated or the apparatus can be connected to the wedge-shaped optical probe 200.

Figure 7:
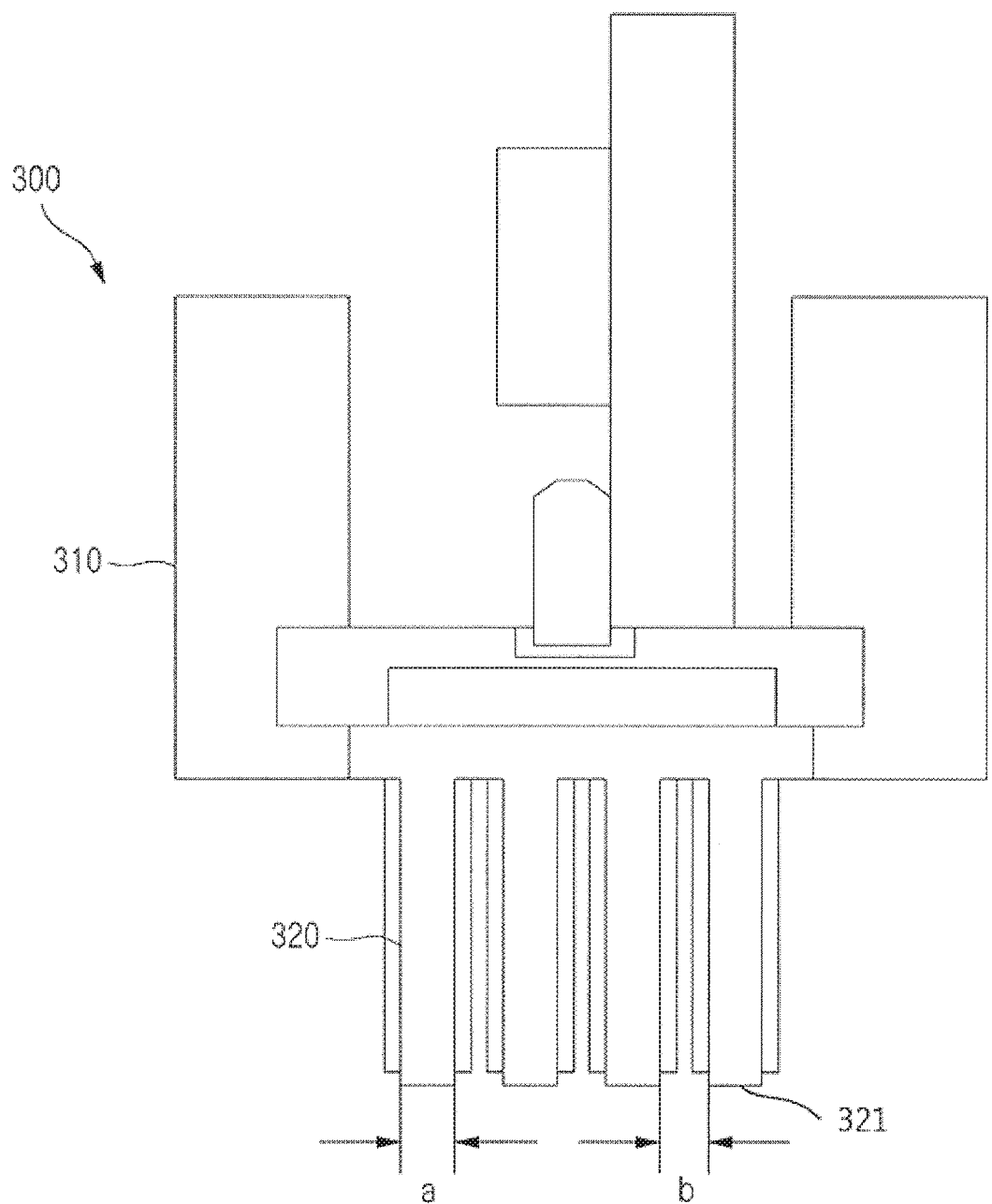
FIG. 7 shows a toothbrush-shaped optical probe for removing strands of hair according to one embodiment of the present invention.

FIG. 7 shows a toothbrush-shaped optical probe for removing strands of hair according to one embodiment of the present invention.

Referring to FIG. 7, a toothbrush-shaped optical probe 300 for removing strands of hair may comprise a main body 310 and a light guide 320.

The main body 310 may accommodate a sensor. Further, the sensor may comprise an amplifier module PCB.

The light guide 320 may be formed at a lower end part of the main body 310, and may be configured with a plurality of threads to which light is transmitted. At this point, the plurality of threads may be configured in the form of a toothbrush shape, and a depression between adjacent threads among the plurality of threads may be formed with a width capable of accommodating strands of hair, thereby coming into close contact with scalp of a user. For instance, a width b of the depression between the adjacent treads may be formed with 0.56 millimeters (mm), and a width a of each of the plurality of threads may be also formed with 0.56 mm.

Further, the light guide 320 may be configured with acrylic optical fiber capable of enabling light to be transmitted, but it has no limitation in material. Here, an outer circumferential surface of the light guide 320 may prevent light from being transmitted, and only a leading end part 321 of the light guide 320 may enable the light to be transmitted.

That is, the light may be incident into the light guide using the acrylic optical fiber without removing the strands of hair.

As is described above, the toothbrush-shaped optical probe 300 for removing strands of hair may push and insert the light guide 320 between the strands of hair as like a toothbrush shape, thereby effectively coming into contact with the scalp.

Further, only the leading end part 321 of the light guide 320 has light transmittance and the outer circumferential surface of the light guide 320 except for the leading end part 321 prevents light from being transmitted, so that light incident into the leading end part 321 may pass the strands of hair to reach the sensor.

Therefore, a structure having a shape capable of pushing and inserting the light guide up to the scalp may be formed by manufacturing the depression that is wider than a thickness of each of the strands of hair, and a thread of the plurality of light guides may be formed, thereby increasing an area coming into contact with the scalp.

As is described above, a signal may be effectively extracted by exposing scalp and enabling a probe to come into close contact with the scalp using an apparatus for removing strands of hair from a near-infrared spectroscopy according to the present invention.

Further, a brain activation image may be efficiently measured by manufacturing a structure having a wedge shape, a toothbrush shape, and the like which are capable of enabling a probe form to reach up to scalp and by increasing an area coming into contact with the scalp.

Although the embodiments have been described in terms of the limited embodiments and drawings, those skilled in the art can make various modifications and changes from the above description. For example, appropriate results can be achieved even if the described techniques are performed in a different order than the described methods, and/or components of the described systems, structures, devices, circuits, and the like are coupled or combined in a different form than the described methods, or changed to or replaced with other components or equivalents.

Therefore, other implementations, other embodiments, and equivalents to the appended claims also fall within the scope of the following claims.

What is claimed is:

1. An apparatus for removing strands of hair from a near-infrared spectroscopy, comprising:
   a main body configured to be worn on a head of a user;
   a plurality of protrusions formed at an inner surface of the main body, and configured to expose a portion of scalp by separating the strands of hair; and
   a probe configured to accommodate a near-infrared spectroscopy sensor thereinside and be directly disposed on the inner surface of the main body and spaced apart from the plurality of protrusions of the main body, the probe including a wedge-shaped surface,
   wherein the strands of hair are separated to both sides of each of the plurality of protrusions such that the portion of the scalp is exposed and come into contact with the wedge-shaped surface of the probe, and
   wherein one of the plurality of protrusions protrudes from the inner surface in a first direction, the probe protrudes from the inner surface in the first direction, and the one of the plurality of the protrusions has a fixed position relative to the probe.

2. The apparatus of claim 1, wherein the probe is formed in plural number and respectively disposed at the main body and spaced apart from the plurality of protrusions of the main body.

3. The apparatus of claim 2, wherein in the main body, a plurality of holes are respectively formed at the main body and spaced apart from the plurality of protrusions, and the probes are respectively coupled to the plurality of holes in an insertion manner.

4. The apparatus of claim 1, wherein the near-infrared spectroscopy sensor is configured with a rectangular printed circuit board (PCB) in which a vertical length is longer than a horizontal length.

* * * * *